US00PP36970P2

(12) United States Plant Patent
Bignozzi

(10) Patent No.: US PP36,970 P2
(45) Date of Patent: Sep. 16, 2025

(54) ***PORTULACA* PLANT NAMED 'LAZZPOR5316'**

(50) Latin Name: ***Portulaca umbraticola* Kunth**
Varietal Denomination: LAZZPOR5316

(71) Applicant: LAZZERI GENETICA S.A.S. DI DALLAGO FRANCO & C., Merano (IT)

(72) Inventor: Luana Bignozzi, Merano (IT)

(73) Assignee: LAZZERI GENETICA S.A.S. DI DALLAGO FRANCO & C., Merano (IT)

( * ) Notice: Subject to any disclaimer, the term of this patent is extended or adjusted under 35 U.S.C. 154(b) by 0 days.

(21) Appl. No.: 19/071,224

(22) Filed: Mar. 5, 2025

(51) Int. Cl.
*A01H 5/02* (2018.01)
*A01H 6/00* (2018.01)

(52) U.S. Cl.
USPC ..... Plt./471

(58) Field of Classification Search
USPC ..... Plt./263.1, 471
See application file for complete search history.

(56) References Cited

U.S. PATENT DOCUMENTS

PP35,593 P2 * 1/2024 Winslow ..... A01H 6/00
Plt./471

* cited by examiner

*Primary Examiner* — Karen M Redden
(74) *Attorney, Agent, or Firm* — C. Anne Whealy

(57) ABSTRACT

A new and distinct cultivar of *Portulaca* plant named 'LAZZPOR5316', characterized by its upright to outwardly spreading and uniformly mounding plant habit; relatively vigorous growth habit and moderate growth rate; freely branching habit; dense and bushy appearance; early and freely flowering habit; long flowering period; bright golden yellow-colored flowers that remain open for an extended period of time during the daytime; and excellent container and garden performance.

2 Drawing Sheets

Figure 1:
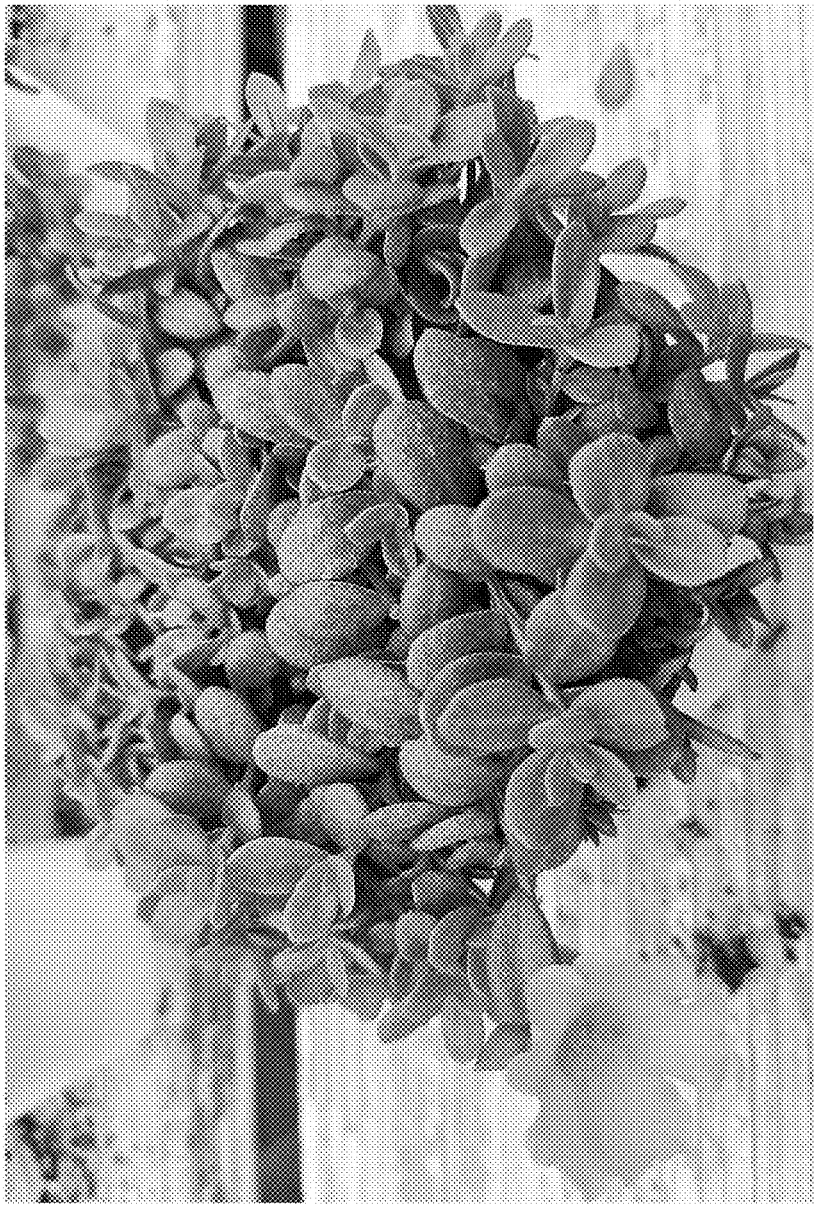

Botanical designation: *Portulaca umbraticola* Kunth.
Cultivar denomination: 'LAZZPOR5316'.

BACKGROUND OF THE INVENTION

The present invention relates to a new and distinct cultivar of *Portulaca* plant, botanically known as *Portulaca umbraticola* Kunth, commonly known as Wingpod Purslane and hereinafter referred to by the name 'LAZZPOR5316'.

The new *Portulaca* plant is a product of a planned breeding program conducted by the Inventor in Merano and Sabaudia, Italy. The objective of the breeding program is to create new uniform *Portulaca* plants with large attractive flowers that remain open for an extended period of time during the daytime and are suitable as container and landscape plants.

The new *Portulaca* plant originated from a cross-pollination made by the Inventor in Merano, Italy in July 2020 of a proprietary selection of *Portulaca umbraticola* Kunth identified as code number 07/224-1, not patented, as the female, or seed, parent with a proprietary selection of *Portulaca umbraticola* Kunth identified as code number 09/52-2, not patented, as the male, or pollen, parent. The new *Portulaca* plant was discovered and selected by the Inventor as a flowering plant from within the progeny of the stated cross-pollination in a controlled greenhouse environment in Sabaudia, Italy in July 2023.

Asexual reproduction of the new *Portulaca* plant by vegetative terminal cuttings in a controlled greenhouse environment in Sabaudia, Italy since August 2023, has shown that the unique features of this new *Portulaca* plant are stable and reproduced true to type in successive generations.

SUMMARY OF THE INVENTION

Plants of the new *Portulaca* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'LAZZPOR5316'. These characteristics in combination distinguish 'LAZZPOR5316' as a new and distinct *Portulaca* plant:

1. Upright to outwardly spreading and uniformly mounding plant habit.
2. Relatively vigorous growth habit and moderate growth rate.
3. Freely branching habit; dense and bushy appearance.
4. Early and freely flowering habit.
5. Long flowering period.
6. Bright golden yellow-colored flowers that remain open for an extended period of time during the daytime.
7. Excellent container and garden performance.

Plants of the new *Portulaca* can be compared to plants of the female parent selection. Plants of the new *Portulaca* differ primarily from plants of the female parent selection in the following characteristics:

1. Plants of the new *Portulaca* are more vigorous than and not as compact as plants of the female parent selection.
2. Plants of the new *Portulaca* have larger flowers than plants of the female parent selection.
3. Flowers of plants of the new *Portulaca* are bright golden yellow in color whereas flowers of plants of the female parent selection are creamy white and red bi-colored.

Plants of the new *Portulaca* can be compared to plants of the male parent selection. Plants of the new *Portulaca* differ primarily from plants of the male parent selection in the following characteristics:

1. Plants of the new *Portulaca* are more vigorous than and not as compact as plants of the male parent selection.
2. Plants of the new *Portulaca* have larger flowers than plants of the male parent selection.
3. Flowers of plants of the new *Portulaca* are bright golden yellow in color whereas flowers of plants of the male parent selection are magenta in color.

Plants of the new *Portulaca* can be compared to plants of the *Portulaca umbraticola* Kunth 'Duna Yellow', not patented. In side-by-side comparisons, plants of the new *Portulaca* differ primarily from plants of 'Duna Yellow' in the following characteristics:

1. Plants of the new *Portulaca* are more vigorous than plants of 'Duna Yellow'.
2. Plants of the new *Portulaca* are more freely flowering than plants of 'Duna Yellow'.
3. Flowers of plants of the new *Portulaca* remain open for a longer period of time during the daytime than flowers of plants of 'Duna Yellow'.
4. Flowers of plants of the new *Portulaca* are bright golden yellow in color whereas flowers of plants of 'Duna Yellow' are greenish yellow in color.

BRIEF DESCRIPTION OF THE PHOTOGRAPHS

The accompanying colored photographs illustrate the overall appearance of the new *Portulaca* plant showing the colors as true as it is reasonably possible to obtain in colored reproductions of this type. Colors in the photographs may differ slightly from the color values cited in the detailed botanical description which accurately describe the colors of the new *Portulaca* plant.

The photograph on the first sheet (FIG. 1) is a side perspective view of a typical flowering plant of 'LAZZPOR5316' grown in a container.

Figure 2:
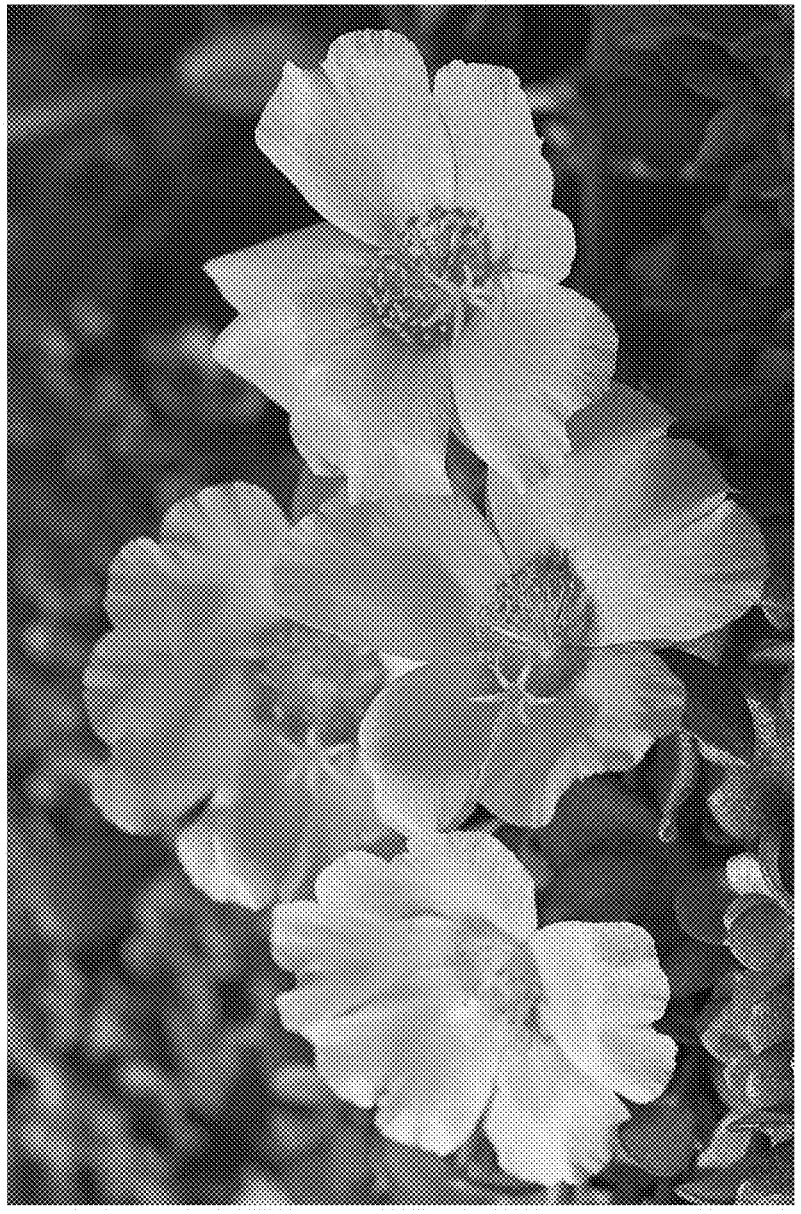

The photograph on the second sheet (FIG. 2) is a close-up view of typical flowers of 'LAZZPOR5316'.

DETAILED BOTANICAL DESCRIPTION

The aforementioned photographs and following observations and measurements describe plants grown during the winter in 15-cm containers in a glass-covered greenhouse in Sabaudia, Italy and under cultural practices typical of commercial *Portulaca* production. During the production of the plants, day temperatures ranged from 23° C. to 25° C., night temperatures ranged from 14° C. to 17° C., and light levels ranged from 60 to 70 klux. Plants were five months from planting rooted young plants when the photographs and the detailed description were taken. In the following description, color references are made to The Royal Horticultural Society Colour Chart, 1995 Edition, except where general terms of ordinary dictionary significance are used.

Botanical classification: *Portulaca umbraticola* Kunth 'LAZZPOR5316'.

Parentage:

*Female, or seed, parent*.—Proprietary selection of *Portulaca umbraticola* Kunth identified as code number 07/244-1, not patented.

*Male or pollen parent*.—Proprietary selection of *Portulaca umbraticola* Kunth identified as code number 09/52-2, not patented.

Propagation:

*Type*.—By vegetative terminal cuttings.

*Time to initiate roots, summer*.—About two weeks at temperatures ranging from 20° C. to 38° C.

*Time to initiate roots, winter*.—About 20 days at temperatures ranging from 14° C. to about 20° C.

*Time to produce a rooted young plant, summer*.—About three weeks at temperatures ranging from 20° C. to 38° C.

*Time to produce a rooted young plant, winter*.—About 30 days at temperatures ranging from 14° C. to about 20° C.

*Root description*.—Medium in thickness, fibrous; typically white to cream in color, actual color of the roots is dependent on substrate composition, water quality, fertilizers, substrate temperature and age of roots.

*Rooting habit*.—Moderately freely branching; medium density.

Plant description:

*Plant and growth habit*.—Upright to outwardly spreading and uniformly mounding plant habit; relatively vigorous growth habit and moderate growth rate; dense and bushy appearance.

*Branching habit*.—Freely branching habit about five to six primary lateral branches per plant each with about three secondary lateral branches developing potentially at every node; pinching enhances branching potential.

*Plant height*.—About 11 cm to 12 cm.

*Plant diameter* (*area of spread*).—About 18 to 19 cm.

Lateral branch description:

*Length*.—About 11 cm to 12 cm.

*Diameter*.—About 5 mm.

*Internode length*.—About 3 cm.

*Strength*.—Strong; flexible.

*Aspect*.—On average, about 45° from vertical.

*Texture and luster*.—Smooth, glabrous; glossy.

*Color, developing*.—Close to 175A.

*Color, developed*.—Close to 177A.

Leaf description:

*Arrangement*.—Opposite, simple.

*Length*.—About 2.5 cm to 3 cm.

*Width*.—About 1.5 cm.

*Shape*.—Oval.

*Apex*.—Rounded.

*Base*.—Narrowly cuneate.

*Margin*.—Entire.

*Texture and luster, upper and lower surfaces*.—Smooth, glabrous; fleshy, succulent; glossy.

*Venation pattern*.—Pinnate.

*Color*.—Developing leaves, upper surface: Close to 137B. Developing leaves, lower surface: Close to 137C. Fully expanded leaves, upper surface: Close to 137A; venation, close to 137D. Fully expanded leaves, lower surface: Close to 138B; venation, close to 138B.

*Petioles*.—Length: About 2 mm. Diameter: About 3 mm. Texture and luster, upper and lower surfaces: Smooth, glabrous; glossy. Strength: Strong. Color, upper surface: Close to 137C. Color, lower surface: Close to 139C.

Flower description:

*Flower arrangement*.—Single rotate and cupped flowers; freely flowering habit with about 120 to 130 flowers per plant during the flowering season; flowers nodding.

*Fragrance*.—Fragrant; pleasant, floral.

*Natural flowering season*.—Plants begin flowering about six to eight weeks after planting; in the garden, plants flower continuously from early spring until the autumn in Italy.

*Flower longevity*.—Depending on temperature, flowers last about two to three days on the plant; flowers persistent; flowers remain open for an extended period of time during the daytime.

*Flower buds*.—Length: About 5 mm. Diameter: About 5 mm. Shape: Ovoid. Texture and luster: Smooth, glabrous; glossy. Color, developing sepals: Close to 146B.

*Flower diameter*.—About 3 cm.

*Flower length* (*height*).—About 2 cm.

*Petals*.—Quantity per flower: Corolla consists of four or five petals in a single whorl; petals imbricate. Length: About 1.5 cm to 1.7 cm. Width: About 1.8 cm to 2 cm. Shape: Obovate. Apex: Rounded and emarginate. Base: Narrow cuneate. Margin: Mostly entire; slightly undulate. Texture and luster, upper surface: Smooth, glabrous, satiny; lossy. Texture and luster, lower surface: Smooth, glabrous; matte. Color: When opening, upper surface: Close to 15C. When opening, lower surface: Close to 14B. Fully opened, upper surface: Close to 17B; venation, close to 17B; color becoming closer to 21A with subsequent development. Fully opened, lower surface: Close to 17C; venation, close to 17C; color becoming closer to 21C with subsequent development.

*Sepals*.—Quantity per flower: Two fused into a tubular calyx. Length: About 5 mm. Width: About 4 mm. Shape: Broadly deltoid. Apex: Acute. Margin: Entire. Texture and luster, upper and lower surfaces: Rugose, glabrous; matte. Color: When opening, upper and lower surfaces: Close to 147B. Fully opened, upper and lower surfaces: Close to 147A.

*Peduncles*.—Length: About 3 mm. Diameter: About 2 mm. Strength: Strong, flexible. Aspect: About 45° from lateral branch axis. Texture and luster: Smooth, glabrous; glossy. Color: Close to 143C.

*Reproductive organs*.—Androecium: Quantity of stamens per flower: About 18 to 22. Filament length: About 2 mm. Filament color: Close to 14A. Anther shape: Oval. Anther length: About 1 mm. Anther color: Close to 23A. Amount of pollen: Abundant. Pollen color: Close to 16A. Gynoecium: Pistil length: About 3 mm. Style length: About 2 mm. Style color: Close to 14B. Stigma diameter: About 3 mm. Stigma shape: Lobed. Stigma color: Close to 21A. Ovary color: Close to 18D. Fruits and seeds: To date, fruit and seed development have not been observed on plants of the new *Portulaca*.

Garden performance: Plants of the new *Portulaca* have been observed to have excellent garden performance and to tolerate temperatures ranging from about 10° C. to about 40° C.

Pathogen & pest resistance: To date, plants of the new *Portulaca* have not been shown to be resistant to pathogens and pests common to *Portulaca* plants.

It is claimed:

1. A new and distinct *Portulaca* plant named 'LAZZPOR5316' as herein illustrated and described.

* * * * *